United States Patent
Joe et al.

(10) Patent No.: US 9,259,718 B1
(45) Date of Patent: Feb. 16, 2016

(54) METHOD FOR PREPARING CATALYST FOR GLYCERIN DEHYDRATION, AND METHOD FOR PREPARING ACROLEIN

(71) Applicant: LG CHEM, LTD., Seoul (KR)

(72) Inventors: Wang Rae Joe, Daejeon (KR); Jun Seon Choi, Daejeon (KR); Ji Yeon Kim, Daejeon (KR); Joo Young Cheon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/432,005

(22) PCT Filed: Jun. 20, 2014

(86) PCT No.: PCT/KR2014/005486
§ 371 (c)(1),
(2) Date: Mar. 27, 2015

(87) PCT Pub. No.: WO2015/072643
PCT Pub. Date: May 21, 2015

(30) Foreign Application Priority Data

Nov. 13, 2013 (KR) .................. 10-2013-0137717

(51) Int. Cl.
| | | |
|---|---|---|
| *C07C 45/00* | (2006.01) | |
| *B01J 27/00* | (2006.01) | |
| *B01J 37/00* | (2006.01) | |
| *C01B 25/00* | (2006.01) | |
| *B01J 27/182* | (2006.01) | |
| *C01B 25/37* | (2006.01) | |
| *B01J 37/28* | (2006.01) | |
| *B01J 37/08* | (2006.01) | |
| *C07C 45/51* | (2006.01) | |

(52) U.S. Cl.
CPC .............. *B01J 27/182* (2013.01); *B01J 37/08* (2013.01); *B01J 37/28* (2013.01); *C01B 25/37* (2013.01); *C07C 45/512* (2013.01)

(58) Field of Classification Search
CPC ....... C07C 45/512; B01J 27/16; B01J 27/182; B01J 37/08; B01J 37/28; C01B 25/32
USPC .................................. 568/486; 502/208, 304
See application file for complete search history.

(56) References Cited

U.S. PATENT DOCUMENTS

| | | | | |
|---|---|---|---|---|
| 7,122,581 | B1 * | 10/2006 | Braconnier | ........ B01J 13/0013 516/89 |
| 7,847,131 | B2 * | 12/2010 | Arita | .................. B01J 27/1804 568/486 |
| 2011/0082319 | A1 | 4/2011 | Dubois | |
| 2013/0018161 | A1 | 1/2013 | Ezawa et al. | |

FOREIGN PATENT DOCUMENTS

| | | |
|---|---|---|
| JP | 2010-095484 A | 4/2010 |
| JP | 2010-253374 A | 11/2010 |
| JP | 2012-091157 A | 5/2012 |
| JP | 2012-091158 A | 5/2012 |
| JP | 4991471 B2 | 8/2012 |
| KR | 10-2011-0011603 A | 2/2011 |
| KR | 10-2011-0016969 A | 2/2011 |
| KR | 10-2012-0093853 A | 8/2012 |
| KR | 10-2013-0029654 A | 3/2013 |

* cited by examiner

*Primary Examiner* — Sikarl Witherspoon
(74) *Attorney, Agent, or Firm* — Dentons US LLP

(57) ABSTRACT

The present invention relates to a method for preparing a catalyst for glycerin dehydration, a catalyst for glycerin dehydration prepared thereby, and a method for preparing acrolein. More particularly, the catalyst for glycerin dehydration prepared by the preparation method is able to minimize by-product formation to improve acrolein selectivity and to maintain high catalytic activity during the reaction.

16 Claims, No Drawings

METHOD FOR PREPARING CATALYST FOR GLYCERIN DEHYDRATION, AND METHOD FOR PREPARING ACROLEIN

This application is a National Stage Entry of International Application No. PCT/KR2014/005486, filed on Jun. 20, 2014, which claims priority to and the benefit of Korean Patent Application No. 10-2013-0137717, filed on Nov. 13, 2013, all of which are hereby incorporated herein by reference in their entirety.

TECHNICAL FIELD

The present invention relates to a method for preparing a catalyst for dehydration and a method for preparing acrolein, and particularly, to a method for preparing a catalyst for glycerin dehydration, which is able to minimize by-product formation to improve acrolein selectivity and to maintain high catalytic activity during the reaction, and a method for preparing acrolein.

BACKGROUND OF ART

Acrolein is a simple unsaturated aldehyde compound including an incomplete reactive group and having high reactivity, and the main uses thereof are as an intermediate in the synthesis of numerous compounds. In particular, acrolein has been widely used as an intermediate in the synthesis of acrylic acid and its esters, superabsorbent polymers, animal feed supplements, food supplements, etc.

Conventionally, acrolein has been prepared by a selective gas-phase oxidation reaction with atmospheric oxygen using a starting material, propylene, which is obtained from the processing of petroleum. However, as reduction in fossil fuels and environmental problems such as the greenhouse effect gradually emerge, many studies have been conducted on a synthetic method of producing acrolein using renewable non-fossil fuel based raw materials.

Accordingly, a natural product, glycerin, obtained as a by-product of biodiesel production, has gained much interest as a raw material for acrolein synthesis. In particular, as the production of biodiesel increases, the glycerin market is expanding, and due to reduction of glycerin price, industrial applications thereof have been studied.

For example, there is known a method of obtaining acrolein by dehydration of glycerin in the presence of a catalyst, and the method is known to be performed by using an acidic catalyst such as zeolite, phosphorus oxide, and tungstophosphoric acid ($H_3PW_{12}O_4$).

However, since the catalysts which were previously used to prepare acrolein from glycerin produce by-products such as hydroxy acetone, hydroxy propanone, propane aldehyde, acetaldehyde, acetone, and polycondensation products of glycerin, there is a limitation in the use of the catalysts for the production of acrolein with high purity. Further, there is a problem that when the catalyst is supported on a carrier, the catalytic activity is rapidly reduced.

Accordingly, there is a demand to develop a method for preparing a catalyst for glycerin dehydration, which is able to minimize by-product formation to improve selectivity and purity of acrolein and conversion ratio and reaction yield of glycerin, and to maintain high catalytic activity even though supported on a carrier.

DETAILED DESCRIPTION OF THE INVENTION

Technical Problem

The present invention provides a method for preparing a catalyst for glycerin dehydration, which is able to minimize by-product formation to improve acrolein selectivity and to maintain high catalytic activity.

Further, the present invention provides a method for preparing acrolein using the catalyst for glycerin dehydration.

Technical Solution

The present invention provides a method for preparing a catalyst for glycerin dehydration, including the steps of reacting a cerium precursor with a solid acid; and reacting a reaction product of the cerium precursor and the solid acid with a phosphorus precursor.

Further, the present invention provides a method for preparing acrolein, including the step of reacting glycerin in the presence of the catalyst for glycerin dehydration.

Hereinafter, a method for preparing a catalyst for dehydration and a method for preparing acrolein according to specific embodiments of the present invention will be described in more detail.

According to one embodiment of the present invention, provided is a method for preparing a catalyst for glycerin dehydration, including the steps of reacting a cerium precursor with a solid acid; and reacting a reaction product of the cerium precursor and the solid acid with a phosphorus precursor.

The present inventors recognized that the previous catalysts used for preparation of acrolein from glycerin produce by-products such as polycondensation products, and thus there is a limitation in the use of the catalysts for the production of acrolein with high purity, and there is also a problem that when the catalyst is supported on a carrier, the catalytic activity is rapidly reduced. Accordingly, the present inventors studied to solve these problems. Consequently, they performed experiments to demonstrate that a catalyst for glycerin dehydration prepared by reacting a cerium precursor with a solid acid and then reacting the product with a phosphorus precursor is able to minimize by-product formation and also prepares acrolein with high yield and high conversion ratio, thereby completing the present invention.

In particular, the method for preparing the catalyst for glycerin dehydration is able to prepare a catalyst which includes a solid acid to be used as a dispersing agent, thereby uniformly dispersing cerium ions serving as active sites therein. Accordingly, the catalyst for glycerin dehydration which is prepared by the above preparation method shows high activity. The catalyst which is prepared by the method for preparing the catalyst for glycerin dehydration may be, for example, in the form of $CePO_4$ or $CePO_4/SiO_2$.

Further, the previous catalysts for glycerin dehydration produce a large amount of by-products such as hydroxy acetone, etc., but the catalyst prepared by the method for preparing the catalyst for glycerin dehydration according to one embodiment improves contact between a reactant and an active phase because the active phase is uniformly dispersed in the catalyst, thereby producing acrolein with a high yield.

In the method for preparing the catalyst for glycerin dehydration according to one embodiment, the step of reacting the cerium precursor and the solid acid may include a sol-gel reaction. The sol-gel reaction may include the step of producing a sol in a suspension state in which colloidal or inorganic unimolecular solid molecules are dispersed, and the step of producing a gel when the sol loses its fluidity resulting from formation of a continuous solid network structure by maintaining the sol reaction to polymerize the dispersed solid molecules.

Specifically, in the catalyst for glycerin dehydration according to one embodiment, the cerium precursor and the solid acid were reacted with each other at a temperature of 50 to 100° C. and at atmospheric pressure for 2 to 10 hours to prepare a sol, and the sol may be in the form in which the cerium precursors are connected between solid acids.

The produced sol is transformed into a gel by heating and drying the sol at a high temperature of 100 to 200° C. so as to prepare a gel-type product of a sol-gel reaction.

In the method for preparing the catalyst for glycerin dehydration, a mixing molar ratio of the cerium precursor and the phosphorus precursor may be 1:1 to 1:10, preferably 1:2 to 1:5. As such, a larger amount of the phosphorus precursor than the cerium precursor is mixed, thereby increasing the production ratio of cerium phosphorus oxide having high activity and inhibiting production of cerium oxide having low activity in a calcination step, and therefore, activity of the catalyst for glycerin dehydration thus prepared can be improved.

The cerium precursor or the phosphorus precursor collectively refers to a substance for providing cerium or phosphorus which is included in the catalyst for glycerin dehydration, and for example, it may be in the form of an oxide or salt containing cerium or phosphorus.

Specifically, the cerium precursor may include one or more selected from the group consisting of cerium nitrate, cerium carbonate, cerium chloride, cerium sulfate, cerium acetate, and mixtures thereof, and use of cerium nitrate is preferred because impurities such as $NO_X$ can be easily separated in the preparation process of the catalyst.

Further, any phosphorus precursor can be used without limitation as long as it is known to be used in the preparation of the catalyst including phosphorus oxide, and for example, $H_3PO_4$, $(NH_3)_2HPO_4$, $(C_2H_5)_3PO_4$, or a mixture thereof may be used.

Citric acid, succinic acid, malic acid, tartaric acid, or a mixture thereof may be used as the solid acid. These solid acids function as a bridge that connects cerium and phosphorus components in the precursor solutions with each other, and therefore, they help prepare a catalyst having active sites which are more uniformly dispersed. As confirmed in experimental examples below, the catalyst for glycerin dehydration of one embodiment which is prepared by using the solid acid is able to exhibit excellent catalytic activity, high glycerin conversion ratio, and high acrolein selectivity, compared to use of alkaline compounds such as ammonia.

The step of reacting the cerium precursor with the solid acid may be conducted by further including a solvent selected from the group consisting of water, alcohols such as methanol or ethanol, and mixtures thereof. In particular, when water is used as the solvent, a sufficient time for gelation of the cerium precursor is provided during evaporation of water, thereby obtaining a catalyst in which the cerium components serving as active sites in the catalyst to be prepared are dispersed uniformly in terms of physicochemical properties.

The method for preparing the catalyst for glycerin dehydration of one embodiment may further include the step of calcinating a product resulting from the reaction of the reaction product of the cerium precursor and the solid acid with the phosphorus precursor.

The calcination step means a series of procedures to prepare a curable material by heating the reaction product at a high temperature, and it may be conducted in a temperature range from 100 to 1200° C., preferably from 500 to 1000° C. If the temperature is lower than the above range, the structure and crystallinity of the catalyst may change during reaction to deteriorate the catalytic activity. If the temperature is higher than the above range, the pore structure or the specific surface area may be reduced to deteriorate the catalytic activity.

Further, the calcination step may be conducted for 10 minutes to 10 hours. If the calcination time is too short, the catalyst may not be completely dried and calcined. If the calcination time is too long, many side-reactions such as carbonization of the catalyst may occur.

The drying step may be further included before the step of calcinating the product resulting from the reaction of the reaction product of the cerium precursor and the solid acid with the phosphorus precursor. In the drying step, a drying method and a drier which are known to be typically used may be used, and for example, the drying step may be conducted using a heat source such as a hot air generator, an oven, a heating plate, etc.

Meanwhile, the method for preparing the catalyst for glycerin dehydration of one embodiment may further include the step of supporting the product, which is obtained from the reaction of the reaction product of the cerium precursor and the solid acid with the phosphorus precursor, on a carrier. The step of supporting the reaction product on the carrier may be performed by using a method known to be used in the art without limitation, and this step may be included in order to more easily store and transport the catalyst for glycerin dehydration and to increase its surface area for improvement of the reaction activity.

The step of supporting the reaction product of the cerium precursor and the solid acid on a carrier may be included, before the step of supporting the product, which is obtained from the reaction of the reaction product of the cerium precursor and the solid acid with the phosphorus precursor, on a carrier. That is, the cerium precursor and the solid acid are reacted, the reaction product thereof is supported on a carrier, and then the resultant is reacted with the phosphorus precursor, followed by further supporting on a carrier.

In particular, when the catalyst for glycerin dehydration prepared according to the conventional preparation method is supported on a carrier, its reaction activity is greatly reduced, compared to the catalyst before being supported, so as to generate a problem of performance reduction. In the above method for preparing the catalyst for glycerin dehydration, however, the cerium precursor and the solid acid are first reacted, and then supported on a carrier, thereby maintaining high reaction activity of the supported catalyst. The solid acid functions as a dispersing agent to connect the cerium precursor and the carrier, leading to uniform dispersion of the active phase of cerium in the carrier. Also, the solid acid functions to improve the viscosity of the resulting solution from the reaction with the cerium precursor, leading to uniform dispersion of the active phase of cerium within the pores of the carrier.

Any carrier may be used without particular limitation, as long as it is known to be used in the typical catalyst. Specific examples of the carrier may include silica, alumina, silica-alumina, titania, zeolite, activated carbon, clay, zirconia, magnesia, magnesium aluminate, calcium aluminate, silicon carbide, zirconium phosphorus oxide, and a mixture thereof, and preferably, silica having a pore size of 20 nm or more.

The carrier may have a specific surface area of 10 to 500 $m^2/g$, and preferably, 50 to 200 $m^2/g$. In particular, the catalyst for glycerin dehydration prepared by supporting the precursor on the carrier having a high specific surface area in the above range has an appropriate pore size, and therefore, deposition of coke can be reduced, and the sufficient catalytic activity can be provided.

According to another embodiment of the present invention, provided is a method for preparing acrolein including the step of reacting glycerin in the presence of the catalyst for glycerin dehydration which is prepared by the method for preparing the catalyst for glycerin dehydration of one embodiment.

As described above, when the catalyst for glycerin dehydration of one embodiment of the present invention is used, dehydration of glycerin may be performed with high acrolein selectivity, and in particular, by-product formation can be minimized, compared to use of other catalysts previously known.

The use of the catalyst for glycerin dehydration may be controlled depending on the amount and concentration of the reactant glycerin, and for example, the catalyst may be fed at a weight hourly space velocity of 10 to 300 mmol/h·$g_{cat}$, and preferably, at a weight hourly space velocity of 10 to 100 mmol/h·$g_{cat}$.

Further, the step of reacting glycerin may be performed at a temperature of 200 to 400° C. Since the step of reacting glycerin is an endothermic reaction, the reaction is preferably performed within the temperature range in order to prepare acrolein with high conversion ratio and selectivity.

Advantageous Effects

According to the present invention, provided are a method for preparing a catalyst for glycerin dehydration, which is able to minimize by-product formation to improve acrolein selectivity and to maintain high catalytic activity during the reaction, and a method for preparing acrolein.

DETAILED DESCRIPTION OF THE EMBODIMENTS

The present invention will be described in more detail with reference to the following examples. However, the following examples are for the illustrative purpose only, and the present invention is not intended to be limited by these examples.

EXAMPLES AND COMPARATIVE EXAMPLES

Preparation of Catalyst for Glycerin Dehydration

Example 1

A predetermined amount (7.723 g) of cerium nitrate (Ce(NO$_3$)$_2$.6H$_2$O, YAKURI, 98.0%) was dissolved in 8 ml of distilled water in a beaker so as to prepare a cerium precursor solution. Further, 3.366 g of citric acid (YAKURI, 99.99%) at the same molar equivalent as cerium nitrate was dissolved in 4 ml of distilled water in another beaker so as to prepare a citric acid solution. Then, the cerium nitrate solution and the citric acid solution thus prepared were mixed with each other, and stirred for 30 minutes to completely mix the two solutions. While the mixed solution was heated and stirred at a temperature of 70° C., distilled water in the solution was evaporated to form a sol, and the sol thus formed was continuously heated for about 3 hours to form a gel. After gel formation, 2.211 g of phosphate (H$_3$PO$_4$ DAEJUNG, 85%) solution at an equivalent weight of 1.1 was added dropwise. Then, the gel was allowed to swell by continuous heating and stirring, and dried in an oven at 170° C. for about 12 hours to completely remove NO gas. Thereafter, the gel was calcined in a furnace under an air atmosphere at 800° C. for 4 hours to prepare a CePO$_4$ catalyst.

Example 2

A predetermined amount (0.565 g) of cerium nitrate (Ce(NO$_3$)$_2$.6H$_2$O, YAKURI, 98.0%) and 0.739 g of citric acid (YAKURI, 99.99%) at the same molar equivalent as cerium nitrate were mixed with each other, and then a cerium precursor and citric acid which were weighed so as to correspond to the pore volume of 2.7 g of silica (SYLOPOL, SP948) as a carrier were dissolved in distilled water. Then, the precursor solution thus prepared was added to 2.7 g of the silica carrier and the solution was allowed to be absorbed into the pores of the carrier by stirring. Thereafter, distilled water remaining in the pores was completely removed by drying in an oven at 110° C. for 5 hours or longer. A phosphate solution prepared by dissolving 2.294 g of phosphate (H$_3$PO$_4$ DAEJUNG, 85%) at an equivalent weight of 2 in distilled water in a volume corresponding to the pore volume of the carrier was also supported in the same manner, and dried in an oven at 110° C. for 12 hours or longer, and then calcined in a furnace under air atmosphere at 800° C. for 4 hours to prepare a 15 wt % CePO$_4$/SiO$_2$ catalyst.

Examples 3 to 5

A 15 wt % CePO$_4$/SiO$_2$ catalyst was prepared in the same manner as in the method for preparing the supported catalyst of Example 2, except that the molar ratio of cerium nitrate and phosphate was changed to 1:3 (Example 3) or 1:4 (Example 4).

Comparative Example 1

A predetermined amount (7.723 g) of cerium nitrate (Ce(NO$_3$)$_2$.6H$_2$O, YAKURI, 98.0%) was dissolved in 20 ml of distilled water in a beaker so as to prepare a cerium precursor solution. Then, a NH$_3$OH solution was added dropwise to the solution at room temperature while stirring to maintain the solution at pH of 8.5. When NH$_3$OH (DAEJUNG, 85%) solution was dripped therein, cerium hydroxide particles were formed to obtain a solution in the slurry type. The solution was stirred for 8 hours, and then 2.211 g of a phosphate (H$_3$PO$_4$ DAEJUNG, 85%) solution was added dropwise. Then, the cerium hydroxide precursor and the phosphate solution were allowed to form a phosphorus oxide solution by stirring for 5 hours. While the solution was washed with distilled water, NH$_3$OH in the catalyst precursor was removed by filtering, and then the resulting precursor was dried in an oven at 110° C. for about 12 hours and calcined under air atmosphere at 800° C. for 4 hours to prepare a CePO$_4$ catalyst.

Comparative Example 2

A CePO$_4$ catalyst was prepared in the same manner as in Comparative Example 1, except that (NH$_3$)$_2$PO$_4$ was used instead of phosphate (H$_3$PO$_4$).

Comparative Example 3

A CePO$_4$ catalyst was prepared in the same manner as in Comparative Example 1, except that (C$_2$H$_5$)$_3$PO$_4$ was used instead of phosphate (H$_3$PO$_4$).

Comparative Example 4

A 15 wt % CePO$_4$/SiO$_2$ catalyst was prepared in the same manner as in the method for preparing the supported catalyst of Example 2, except that the molar ratio of cerium nitrate and phosphate was changed to 1:1.1.

Comparative Example 5

A 15 wt % CePO$_4$/SiO$_2$ catalyst was prepared in the same manner as in the method for preparing the supported catalyst of Example 3, except that no citric acid was added.

TABLE 1

Preparation method of bulk catalyst

| | Preparation method of catalyst | Type of phosphate |
|---|---|---|
| Example 1 | Citric acid sol-gel method | H₃PO₄ |
| Comparative Example 1 | NH₃OH sol-gel method | H₃PO₄ |
| Comparative Example 2 | NH₃OH sol-gel method | (NH₃)₂PO₄ |
| Comparative Example 3 | NH₃OH sol-gel method | (C₂H₅)₃PO₄ |

TABLE 2

Preparation method of SiO₂-supported catalyst

| | Molar ratio of Ce:P | Additive | Solvent |
|---|---|---|---|
| Example 2 | 1:2 | Citric acid | Water |
| Example 3 | 1:3 | Citric acid | Water |
| Example 4 | 1:4 | Citric acid | Water |
| Example 5 | 1:5 | Citric acid | Water |
| Comparative Example 4 | 1:1.1 | Citric acid | Water |
| Comparative Example 5 | 1:3 | None | Water |
| Comparative Example 6 | 1:3 | Citric acid | Ethanol |

Experimental Example

Glycerin Conversion Ratio, and Acrolein and By-Product Selectivity

Acrolein was produced from glycerin using the catalysts prepared in the examples and comparative examples, and an HTS (high-throughput screening) apparatus which was manufactured to evaluate performance with a small amount of the catalyst for a short time under the conditions described in the following Table 3 was used. The products were analyzed in-situ by GC to calculate the conversion ratio, selectivity, and yield. The glycerin conversion ratio and acrolein selectivity are shown in the following Tables 4 and 5.

Herein, the glycerin conversion ratio represents a ratio of glycerin to other compounds converted therefrom, and the acrolein selectivity represents a proportion of acrolein in the converted compounds.

Further, Comparative Selectivity 1 represents a comparison of the selectivity of hydroxy acetone to the selectivity of acrolein and the selectivity of a compound having a molecular weight of 130, and Comparative Selectivity 2 represents a comparison of the selectivity of by-product to the selectivity of acrolein and the selectivity of a compound having a molecular weight of 130. In Comparative Selectivity 1 and 2, hydroxy acetone is the major by-product of glycerin dehydration, and the by-product includes hydroxy acetone, aryl alcohol, acetol, propionic acid, 1,2-propanediol, 1,3-propanediol, and cyclic acetal compounds produced by double condensation/dehydration between glycerin molecules or between acetol and glycerin. In the selectivity of the compound having a molecular weight of 130, the compound having a molecular weight of 130 is a cyclic acetal compound produced by dehydration of acrolein and glycerin, and is a by-product produced in the rear part of the reactor by heating at 200° C.

TABLE 3

Conditions for glycerin dehydration

| Reaction pressure | 1 atm |
|---|---|
| Reaction temperature | 280° C. |
| Feed rate of reactant | 3.5 ml/h |
| Reaction time | 1 hour |
| Glycerin concentration | 28.08 wt % |
| WHSV (weight hourly space velocity) | 113.03 mmol/(h · gcat) |
| Catalyst amount | 0.1 g |

TABLE 4

Glycerin conversion ratio, and Acrolein and Hydroxy acetone selectivity

| Example | Glycerin conversion ratio (%) | Acrolein selectivity (%) | Hydroxy acetone selectivity (%) | Molecular weight 130 selectivity (%) |
|---|---|---|---|---|
| Example 1 | 16.2 | 18.74 | 36.11 | 13.28 |
| Example 2 | 4.21 | 18.51 | 28.00 | 14.29 |
| Example 3 | 16.59 | 19.39 | 20.33 | 19.70 |
| Example 4 | 9.30 | 16.99 | 27.74 | 12.75 |
| Example 5 | 13.82 | 21.56 | 25.51 | 16.05 |
| Comparative Example 1 | 1.22 | 6.72 | 44.77 | 7.14 |
| Comparative Example 2 | 0.75 | 6.04 | 37.84 | 7.80 |
| Comparative Example 3 | 0.78 | 5.09 | 25.01 | 4.64 |
| Comparative Example 4 | 3.74 | 6.31 | 10.22 | 9.13 |
| Comparative Example 5 | 5.40 | 14.98 | 20.38 | 16.35 |
| Comparative Example 6 | 9.80 | 9.97 | 13.98 | 16.74 |

TABLE 5

Comparative selectivity of by-product to acrolein selectivity

| Example | *Comparative Selectivity 1 | **Comparative Selectivity 2 |
|---|---|---|
| Example 1 | 1.93 | 2.73 |
| Example 2 | 1.51 | 2.54 |
| Example 3 | 1.05 | 2.06 |
| Example 4 | 1.63 | 2.97 |
| Example 5 | 1.18 | 2.09 |
| Comparative Example 1 | 6.67 | 9.14 |
| Comparative Example 2 | 6.26 | 9.57 |
| Comparative Example 3 | 4.91 | 12.33 |
| Comparative Example 4 | 1.62 | 7.66 |
| Comparative Example 5 | 1.36 | 3.01 |
| Comparative Example 6 | 1.40 | 4.22 |

*Comparative Selectivity 1 = Selectivity of hydroxy acetone/(Selectivity of acrolein + Selectivity of a compound having a molecular weight of 130)
**Comparative Selectivity 2 = Selectivity of by-product/(Selectivity of acrolein + Selectivity of a compound having a molecular weight of 130)

As shown in Tables 4 and 5, when glycerin was reacted using the catalysts of the examples which were prepared by using the cerium precursor and the phosphorus precursor, and citric acid, the glycerin conversion ratio and the acrolein selectivity were remarkably increased, compared to use of the catalysts of the comparative examples which were prepared by using an alkaline compound such as $NH_3OH$, instead of citric acid.

Further, Comparative Selectivity 1 or 2 which is a comparison of the selectivity of by-products to the selectivity of acrolein which is the desired main product in the above reaction was lower than those obtained by using the catalysts of the comparative examples.

That is, these results showed that the catalysts for glycerin dehydration of the examples are able to produce acrolein from glycerin with high selectivity and high purity, and to inhibit production of by-products such as hydroxy acetone.

The invention claimed is:

1. A method for preparing a catalyst for glycerin dehydration, comprising the steps of:
reacting a cerium precursor with a solid acid; and
reacting a reaction product of the cerium precursor and the solid acid with a phosphorus precursor.

2. The method of claim 1, wherein the step of reacting the cerium precursor and the solid acid includes a sol-gel reaction.

3. The method of claim 2, wherein the sol-gel reaction includes a step of heating at a temperature of 20 to 200° C.

4. The method of claim 1, wherein a mixing molar ratio of the cerium precursor and the phosphorus precursor is 1:1 to 1:10.

5. The method of claim 1, wherein the cerium precursor includes one or more selected from the group consisting of cerium nitrate, cerium carbonate, cerium chloride, cerium sulfate, and cerium acetate.

6. The method of claim 1, wherein the phosphorus precursor includes one or more selected from the group consisting of $H_3PO_4$, $(NH_3)_2HPO_4$, and $(C_2H_5)_3PO_4$.

7. The method of claim 1, wherein the solid acid includes one or more selected from the group consisting of citric acid, succinic acid, malic acid, and tartaric acid.

8. The method of claim 1, wherein the step of reacting the cerium precursor with the solid acid is conducted by further including a solvent selected from the group consisting of water and alcohols.

9. The method of claim 1, further comprising the step of calcinating a product resulting from the reaction of the reaction product of the cerium precursor and the solid acid with the phosphorus precursor.

10. The method of claim 9, wherein the calcination step is conducted in a temperature range from 100 to 1200° C.

11. The method of claim 9, wherein the calcination step is conducted for 10 minutes to 10 hours.

12. The method of claim 1, further comprising the step of supporting a product, which is obtained from the reaction of the reaction product of the cerium precursor and the solid acid with the phosphorus precursor, on a carrier.

13. The method of claim 12, further comprising the step of supporting the reaction product of the cerium precursor and the solid acid on a carrier, before the step of supporting the product, which is obtained from the reaction of the reaction product of the cerium precursor and the solid acid with the phosphorus precursor, on a carrier.

14. The method of claim 12, wherein the carrier is selected from the group consisting of silica, alumina, silica-alumina, titania, zeolite, activated carbon, clay, zirconia, magnesia, magnesium aluminate, calcium aluminate, silicon carbide, and zirconium phosphorus oxide, and mixtures thereof.

15. A method for preparing acrolein, comprising the step of reacting glycerin in the presence of the catalyst for glycerin dehydration prepared by the method of claim 1.

16. The method of claim 15, wherein the dehydration is conducted at a temperature of 200 to 400° C.

\* \* \* \* \*